United States Patent
Yu et al.

(10) Patent No.: US 7,582,310 B2
(45) Date of Patent: Sep. 1, 2009

(54) BIODEGRADABLE AND BIOACTIVE GLASS-CERAMICS, AND METHOD FOR FABRICATING THE SAME

(75) Inventors: Hyun Seung Yu, Seoul (KR); Kug Sun Hong, Seoul (KR); Hwan Kim, Bucheon-si (KR); Dong Ho Lee, Seoul (KR); Choon Ki Lee, Seoul (KR); Bong Soon Chang, Seoul (KR); Deug Joong Kim, Seoul (KR); Jun Hyuk Seo, Seoul (KR); Jae Hyup Lee, Seoul (KR); Ki Soo Park, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 955 days.

(21) Appl. No.: 10/648,217

(22) Filed: Aug. 27, 2003

(65) Prior Publication Data

US 2004/0043053 A1 Mar. 4, 2004

(30) Foreign Application Priority Data

Sep. 2, 2002 (KR) .................. 10-2002-0052566

(51) Int. Cl.
*A61F 2/28* (2006.01)

(52) U.S. Cl. ..................................... 424/426
(58) Field of Classification Search ............... None
See application file for complete search history.

(56) References Cited

U.S. PATENT DOCUMENTS 4,783,429 A * 11/1988 Shibuya et al. .............. 501/5

FOREIGN PATENT DOCUMENTS

WO WO9727148 * 7/1997

* cited by examiner

*Primary Examiner*—Carlos A. Azpuru
(74) *Attorney, Agent, or Firm*—Rosenberg, Klein & Lee

(57) ABSTRACT

Disclosed herein is a biodegradable and bioactive glass-ceramic fabricated by mixing a slowly biodegradable glass-ceramic and a highly biodegradable glass-ceramic in a predetermined mixing ratio wherein the bioactivity is maintained to be constant, and the biodegradation rate is controlled by the mixing ratio. The biodegradable and bioactive glass-ceramic is fabricated from a composition consisting of calcium oxide (CaO), silica ($SiO_2$), boron oxide ($B_2O_3$), magnesium oxide (MgO), calcium fluoride ($CaF_2$) and phosphorus pentoxide ($P_2O_5$).

1 Claim, 11 Drawing Sheets

US 7,582,310 B2

BIODEGRADABLE AND BIOACTIVE GLASS-CERAMICS, AND METHOD FOR FABRICATING THE SAME

BACKGROUND OF THE INVENTION

1. Field of the Invention

The present invention relates to a biodegradable and bioactive glass-ceramic, and a method for fabricating the glass-ceramic. More particularly, the present invention relates to a biodegradable and bioactive glass-ceramic fabricated by mixing a slowly biodegradable glass-ceramic and a highly biodegradable glass-ceramic in a predetermined mixing ratio wherein the bioactivity is maintained to be constant, and the biodegradation rate is controlled by the mixing ratio.

2. Description of the Related Art

The most widely used bioactive glass-ceramic for artificial bones or bone cements is Cerabone-AW®, of which composition is suggested in Japanese Patent Laid-Open No. 03-131263 (1989). The glass-ceramic composition consists of MgO, CaO, $SiO_2$, $P_2O_5$ and $CaF_2$ wherein the weight ratio between the respective components is 4.6:44.7:34.0:16.2:0.5. The glass-ceramic composition is compacted at near 830° C., and oxyfluoroapatite ($Ca_{10}(PO_4)_6(O,F)_2$) and β-wollastonite ($CaSiO_3$) are consecutively crystallized at near 870° C. Since the glass-ceramic exhibits excellent bone conductivity, it can be directly bonded to bones. In addition, since the glass-ceramic has a high compressive stress of 1080 MPa, a high hardness of 680 Hv, a high bending strength of 178 MPa, and a high fracture toughness of 2.0 $MPa \cdot m^{1/2}$, it can be used as artificial vertebra and iliac crests, etc. to which a stress is directly applied.

However, since the glass-ceramic is substantially insoluble in a living body, it cannot be completely replaced by bone for a relatively long period of time.

On the other hand, U.S. Pat. Nos. 4,103,002, 4,234,972, 4,851,046, etc., disclose other bioactive glasses. These glasses are highly bioactive, but have a very low mechanical strength. In addition, the glasses are so readily biodegraded that they are limited in the application to artificial bones.

Presently known and commercially available conventional bioactive glasses and glass-ceramics have a satisfactory mechanical strength, but they have a problem that their biodegradation in the body is too fast or too slow.

SUMMARY OF THE INVENTION

Therefore, the present invention has been made in view of the above problems, particularly slow biodegradability of Cerabone-AW® in spite of a high mechanical strength and osteo-conductivity, and it is an object of the present invention to provide a bioactive glass-ceramic with excellent bioactivity and biodegradability, and a bioactive glass-ceramic fabricated by mixing a highly bioactive and readily biodegradable glass-ceramic powder and a slowly biodegradable glass-ceramic powder in a predetermined mixing ratio, sintering the mixture and crystallizing wherein the biodegradation rate is controlled by the mixing ratio.

In order to accomplish the above object of the present invention, there is provided a biodegradable and bioactive glass-ceramic fabricated from a composition consisting of 41.4~45.75% by weight of calcium oxide (CaO), 35.0~47.62% by weight of silica ($SiO_2$), 1.62~14.58% by weight of phosphorus pentoxide ($P_2O_5$), 0.5~14.58% by weight of boron oxide ($B_2O_3$), 0.46~4.14% by weight of magnesium oxide (MgO) and 0.05~0.45% by weight of calcium fluoride ($CaF_2$).

When the glass-ceramic composition is out of these ranges, a glass formation is difficult or sintering is insufficiently carried out due to too high a crystallization rate. Even though the glass formation is possible and sintering is sufficiently carried out, the glass-ceramic to be fabricated is too slowly biodegraded or too fast biodegraded.

In accordance with one aspect of the present invention, there is provided a biodegradable and bioactive glass-ceramic fabricated by mixing a first glass consisting of 41.03~45.86% by weight of calcium oxide (CaO), 43.97~49.14% by weight of silica ($SiO_2$) and 5~15% by weight of boron oxide ($B_2O_3$), and a second glass consisting of 44.7 parts by weight of calcium oxide (CaO), 44.7 parts by weight of magnesium oxide (MgO), 34.0 parts by weight of silica ($SiO_2$), 16.2 parts by weight of phosphorus pentoxide ($P_2O_5$) and 0.5 parts by weight of calcium fluoride ($CaF_2$) wherein the mixing ratio of the first glass to the second glass is between 90:10 and 10:90 on a weight basis.

In accordance with another aspect of the present invention, there is provided a method for fabricating a biodegradable and bioactive glass-ceramic, comprising: preparing a first glass consisting of CaO, $SiO_2$ and $B_2O_3$ and a second glass consisting of CaO, MgO, $SiO_2$, $P_2O_5$ and $CaF_2$, respectively; pulverizing the first glass and the second glass into finely-divided powders, respectively; mixing the first glass powder and the second glass powder in a mixing ratio of 90:10~10:90 (wt/wt) to obtain a glass powder mixture; molding the glass powder mixture using a press or making a porous body; and heating the molded or porous body at 750~900° C. to sinter and crystallize it.

The biodegradable and bioactive glass-ceramic of the present invention has a composition comprising 41.03~45.86% by weight of calcium oxide (CaO), 43.97~49.14% by weight of silica ($SiO_2$) and 5~15% by weight of boron oxide ($B_2O_3$) (the first glass).

When the content of calcium oxide in the glass-ceramic is less than 41.03% by weight, there is a problem that the glass-ceramic is too fast biodegraded in body fluid. When the content of calcium oxide exceeds 45.86% by weight, the glass formation is impossible. When the content of silica in the glass-ceramic is less than 43.97% by weight, the glass formation is impossible. When the content of silica exceeds 49.14% by weight, there are problems that the glass-ceramic is too fast biodegraded and loses its bioactivity. When the content of boron oxide in the glass-ceramic is less than 5% by weight, the glass-ceramic is too slowly biodegraded in body fluid and thus prevents the bone growth with the lapse of time. When the content of boron oxide exceeds 15% by weight, the glass-ceramic is too fast biodegraded in body fluid due to high water-solubility of boron oxide.

The first glass (hereinafter, referred to as 'CBS glass') is prepared from a composition consisting of 41.03~45.86% by weight of calcium oxide (CaO), 43.97~49.14% by weight of silica ($SiO_2$) and 5~15% by weight of boron oxide ($B_2O_3$). The second glass (hereinafter, referred to as 'CERA glass') is prepared from a composition consisting of 44.7 parts by weight of calcium oxide (CaO), 44.7 parts by weight of magnesium oxide (MgO), 34.0 parts by weight of silica ($SiO_2$), 16.2 parts by weight of phosphorus pentoxide ($P_2O_5$) and 0.5 parts by weight of calcium fluoride ($CaF_2$) and has a composition identical to that of Cerabone-AW®.

The CSB glass is a highly biodegradable glass-ceramic. The composition of CERA glass is identical to that of Cerabone-AW®, and is a part of glass-ceramic compositions disclosed in Japanese Patent Laid-Open No. 3-131263. When the content of calcium oxide in the CSB glass is less than 41.03% by weight, the composition is in the immiscibility region and thus the glass formation is difficult. When the content of calcium oxide exceeds 45.86% by weight, crystallization occurs without glass formation. When the content of silica in the CSB glass is less than 43.97% by weight, the composition is in the immiscibility region and thus the glass formation is difficult. When the content of silica exceeds 49.14% by weight, the glass formation is possible but the bioactivity of the glass to be formed is poor. When the content of boron oxide in the CSB glass is less than 5% by weight, the biodegradability of the glass to be formed is poor and thus the mixture of the CSB and the CERA glass cannot control the biodegradability. When the content of boron oxide exceeds 15% by weight, the composition is in the immiscibility region and thus the glass formation is difficult.

The glass-ceramic thus fabricated is composed of crystalline β-wollastonite ($CaSiO_3$), crystalline fluoroapatite ($Ca_{10}(PO_4)_6(O,F)_2$) and a residual glassy phase.

The relative amount between the two crystalline phases and the amount of the residual glassy phase depend on the mixing ratio. In particular, since the residual glassy phase and β-wollastonite ($CaSiO_3$) have a relatively high biodegradation rate but fluoroapatite is not biodegraded, the biodegradation rate can be appropriately controlled by the relative amount therebetween.

Since the CBS glass powder consisting of 41.03~45.86% by weight of calcium oxide (CaO), 43.97~49.14% by weight of silica ($SiO_2$) and 5~15% by weight of boron oxide ($B_2O_3$) can be sintered at a temperature lower than 800° C. (low-temperature sintering), there are advantages in that the glass-ceramic fabricated by mixing with the CBS glass powder is easily sintered compared to conventional glass-ceramics, and lowers the crystallization temperature of β-wollastonite ($CaSiO_3$) and fluoroapatite ($Ca_{10}(PO_4)_6(O,F)_2$).

The mixing ratio of the CERA glass powder having a composition identical to Cerabone-AW®, to the CBS glass powder is between 90:10 and 10:90 on a weight basis, and preferably 20:80~80:20. When the CBS glass powder is mixed in an amount less than 10% by weight, low biodegradation rate of the Cerabone-AW® glass-ceramic cannot be improved. When the CBS glass powder is mixed in an amount more than 90% by weight, the biodegradation rate is so high that when the glass-ceramic is a porous body, the pore structure may collapse. In addition, there are risks that inflammation may be caused and collapse of pore structure may inhibit bone ingrowth.

The glass powder compacts are fully densified at 700~830° C., thus showing the maximum bulk density, and crystallization follows densification. The sintered glass-ceramic is soaked in simulated body fluid (SBF) for 1 day for bioactivity measurement. As a result, it was observed that hydroxycarbonated apatite (HCA) layers, typically shown in highly bioactive materials, were formed, and the surfaces roughness increased by biodegradation.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Hereinafter, the present invention will be explained in more detail in the following Examples with reference to the accompanying drawings.

Figure 1:
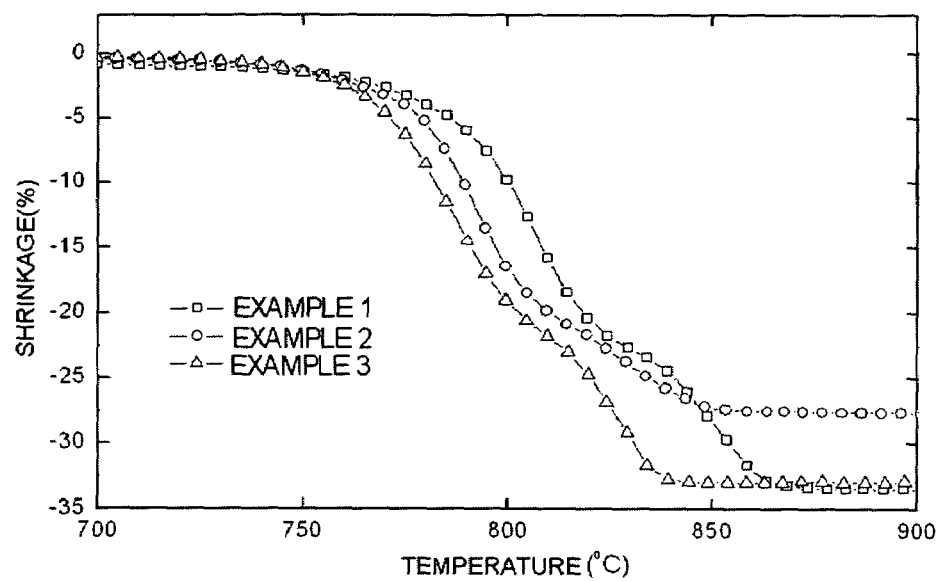
FIG. 1 is a curve showing the shrinkage of glass powder compacts having different compositions with increasing temperature.
Figure 2A:
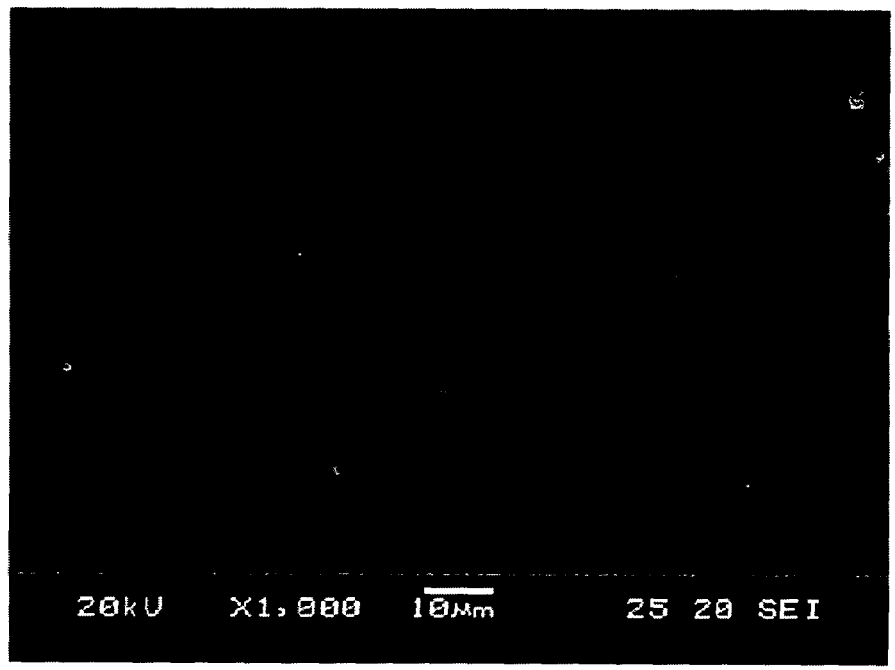
FIGS. 2a to 2c are electron microscope images showing the microstructures of specimens with the maximum bulk density, respectively.
Figure 2B:
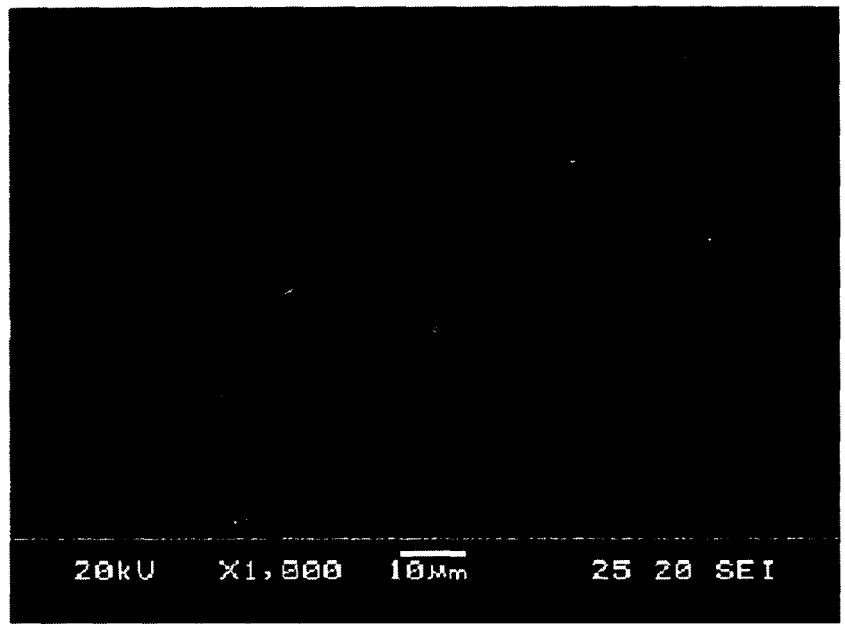
Figure 2C:
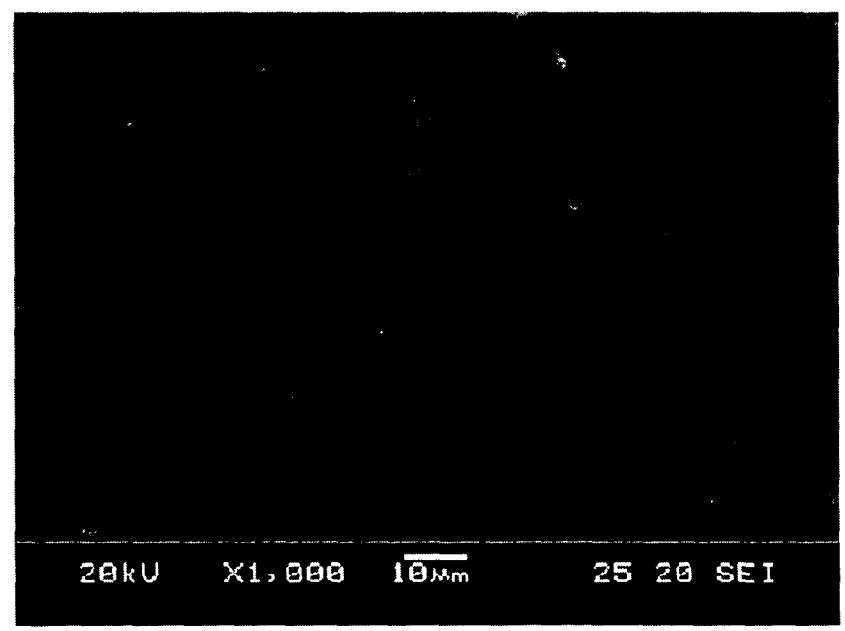
Figure 3A:
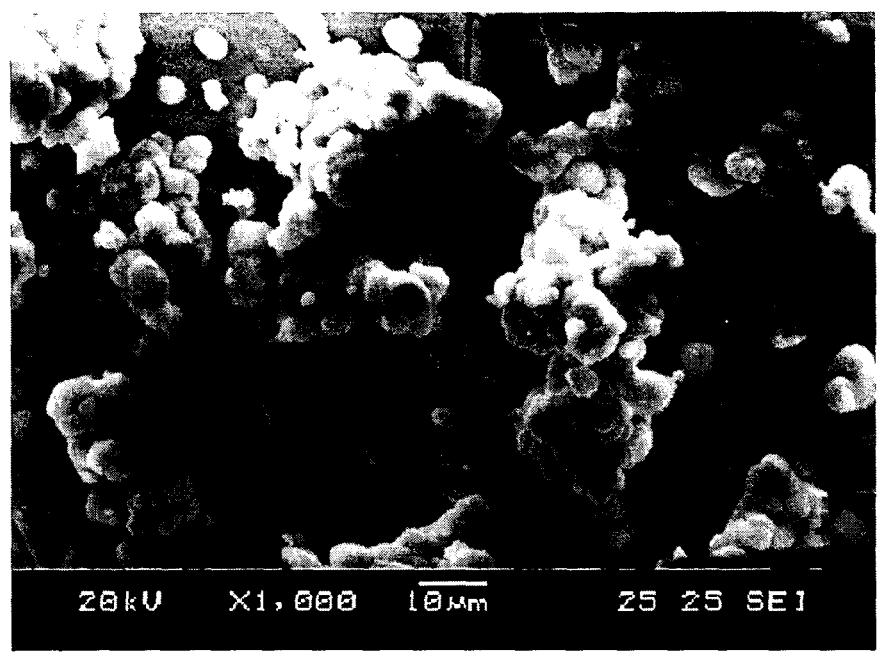
FIGS. 3a to 3c are electron microscope images showing the surfaces of specimens taken out 1 day after soaking polished specimens in simulated body fluid, respectively.
Figure 3B:
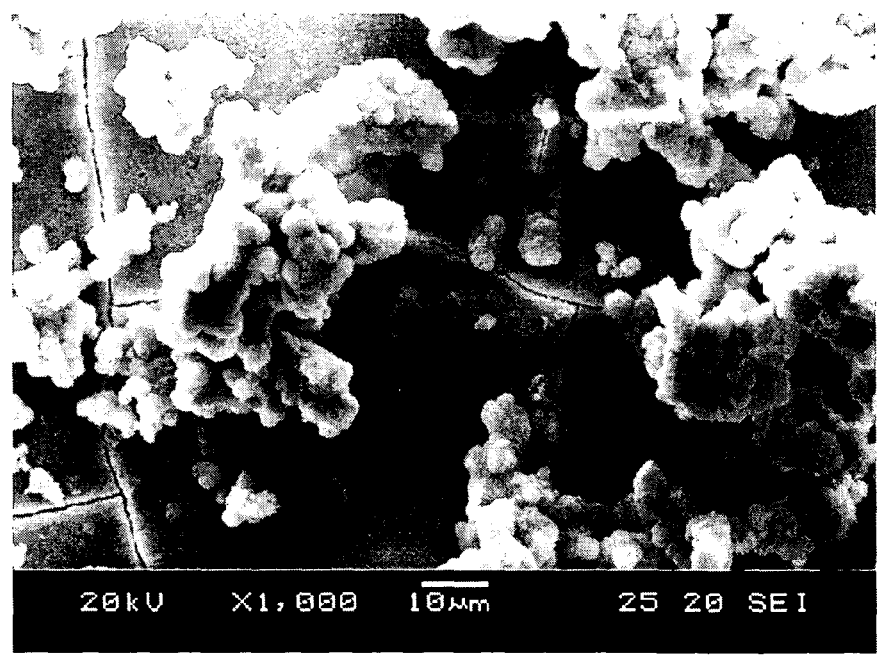
Figure 3C:
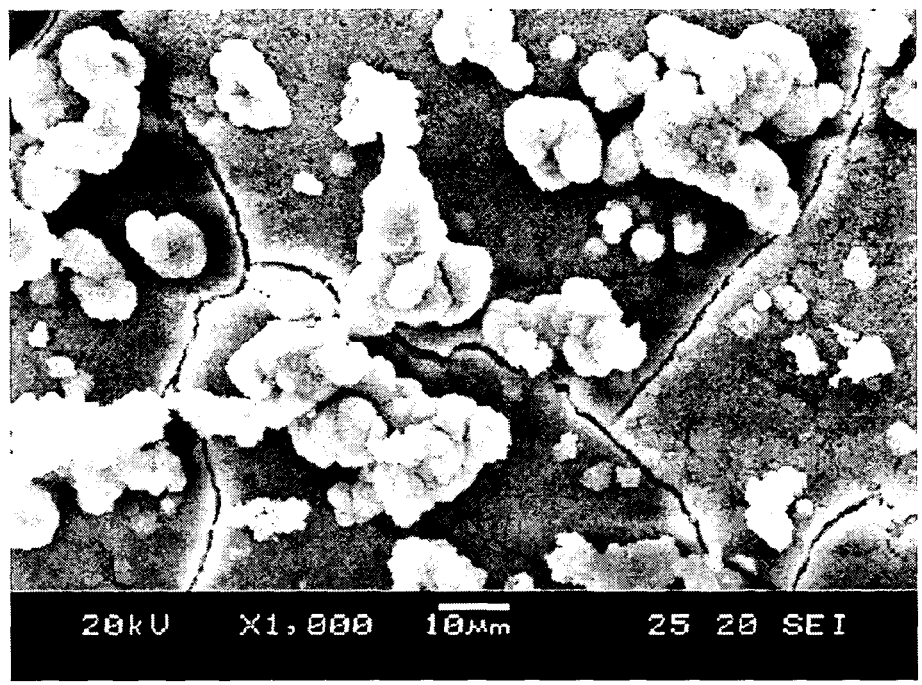
Figure 4:
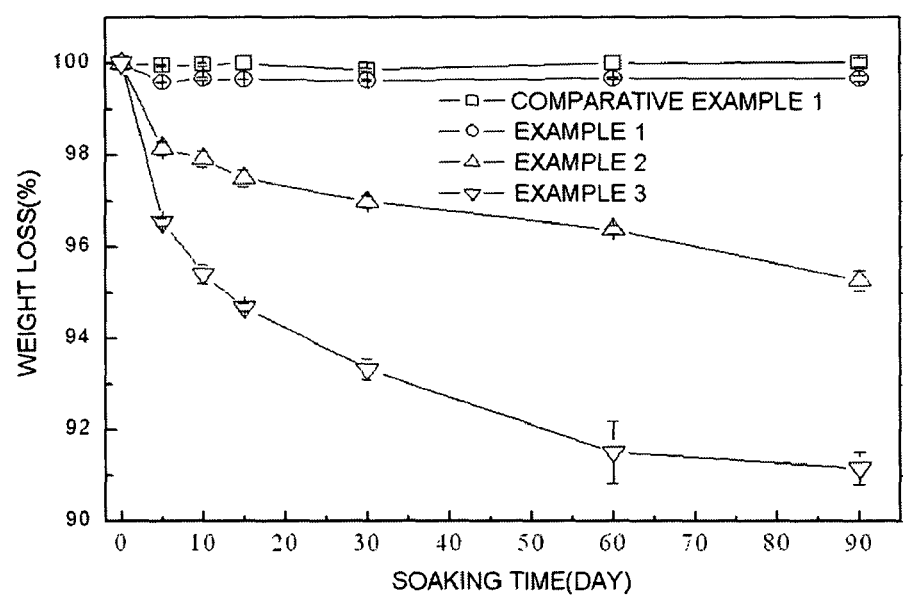
FIG. 4 is a graph showing the weight loss of specimens with increasing soaking time in simulated body fluid.
Figure 5:
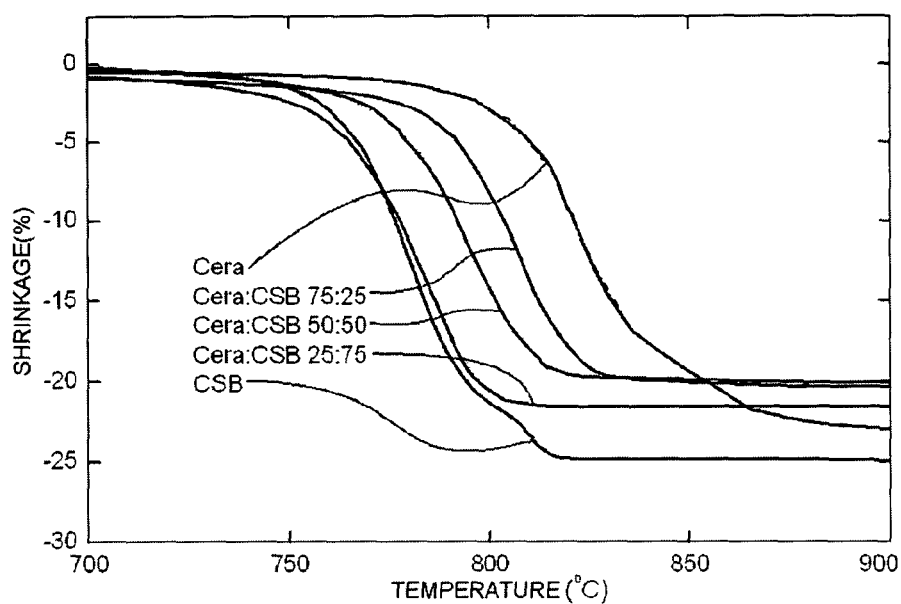
FIG. 5 is a curve showing the shrinkage of glass powder compacts having different mixing ratios of CBS and CERA glass with increasing temperature.

FIG. 1 is a curve showing the shrinkage of glass powder compacts having different compositions shown in Table 1 below with increasing temperature; FIGS. 2a to 2c are electron microscope images showing the microstructures of specimens with the maximum bulk density, respectively; FIGS. 3a to 3c are electron microscope images showing the surfaces of specimens taken out 1 day after soaking polished specimens having the maximum bulk density in simulated body fluid, respectively; and FIG. 4 is a graph showing the weight loss of specimens with increasing soaking time in simulated body fluid;

In addition, FIG. 5 is a curve showing the shrinkage of molded bodies composed of a CBS glass and a CERA glass in different mixing ratios with increasing temperature; FIGS. 6a to 6e are electron microscope images showing the microstructures of specimens with the maximum sintering density, respectively; FIGS. 7a to 7f are electron microscope images showing the surfaces of specimens taken out 1 day after soaking polished specimens in simulated body fluid, respectively; and FIG. 8 is a graph showing the weight loss of specimens with increasing soaking time in simulated body fluid.

Hereinafter, the present invention will be described in more detail with reference to the following Examples. However, these Examples are given for the purpose of illustration and are not to be construed as limiting the scope of the invention.

EXAMPLES 1 to 3

First, calcium carbonate (purity: 99.99%), silica ($SiO_2$) (purity: 99.9%), borate ($B_2O_3$) (purity: 99.9%), magnesium oxide (MgO) (purity: 99.9%), calcium fluoride ($CaF_2$) (purity: 99%) and calcium pyrophosphate ($Ca_2P_2O_7$) (purity: 99.9%) were mixed in accordance with various mixing ratios shown in Table 1 below. The mixture was placed in a platinum crucible, and gradually heated to 1400° C. in an electric furnace. While maintaining the mixture at this temperature for 2 hours, the mixture was completely melted. The molten mixture was taken out of the crucible, poured into a stainless steel mold or a water bath, and rapidly cooled to fabricate a glass. The glass thus fabricated was pulverized into grains below 80 μm, and further pulverized in a planetary mill for 5 hours to obtain a glass powder having a particle size of 1~5 μm.

TABLE 1

Glass Composition of samples (unit: wt %)

|           | CaO   | $SiO_2$ | $P_2O_5$ | MgO  | $CaF_2$ | $B_2O_3$ |
|-----------|-------|---------|----------|------|---------|----------|
| Example 1 | 44.39 | 37.14   | 12.15    | 3.45 | 0.38    | 2.5      |
| Example 2 | 44.07 | 40.28   | 8.1      | 2.3  | 0.25    | 5        |
| Example 3 | 43.76 | 43.41   | 4.05     | 1.15 | 0.13    | 7.5      |

After the obtained glass powder was mixed with 10% by weight of 10 wt % PVA (polyvinyl alcohol) solution to granulate the mixture, the granulated mixture was poured into a stainless steel mold and molded under an appropriate pressure to form a glass powder compact. The glass powder compact was sintered at 700~900° C. for 2 hours. The bulk density and the open porosity of the sintered specimens were measured at various temperatures, and the microstructures of the specimens with the maximum sintering density were determined by scanning electron microscopy (SEM).

The shrinkage curve shown in FIG. 1 reveals that the specimens were sintered at 750~850° C. As shown in FIGS. 2a to 2c, few pores were observed in the microstructures of the specimens having the maximum bulk density, suggesting that the specimens were fully densified. As can be seen from electron microscope images shown in FIGS. 3a to 3c, HCA layers were formed on the entire surfaces of the specimens taken out 1 day after soaking in simulated body fluid. This observation suggests that the specimens are highly bioactive. As can be seen from a weight loss-soaking time curve shown in FIG. 4, as the content of $B_2O_3$ in the specimens increased, the weight of the specimens was greatly reduced. This demonstrates that the biodegradation of the specimens had actively proceeded.

EXAMPLES 4 to 10

First, calcium carbonate ($CaCO_3$) (purity: 99.99%), silica ($SiO_2$) (purity: 99.9%) and borate ($B_2O_3$) (purity: 99.9%) were weighed so that the ratio of $CaO:SiO_2:B_2O_3$ was 43.45%:46.55%:10% on a weight basis, and subjected to a dry mixing process.

The mixture was placed in a platinum crucible, and gradually heated to 1,400° C. While maintaining the mixture at this temperature for 2 hours, the mixture was completely melted. The molten mixture was taken out of the crucible, and poured into a stainless steel mold to fabricate a first glass (CBS glass).

Separately, calcium oxide (CaO) (purity: 99.99%), silica ($SiO_2$) (purity: 99.9%), magnesium oxide (MgO) (purity: 99.9%), calcium fluoride ($CaF_2$) (purity: 99%) and monocalcium phosphate ($Ca_2P_2O_7$) (purity: 99.9%) were weighed so that the ratio of calcium oxide (CaO): magnesium oxide (MgO): silica ($SiO_2$): phosphorus pentoxide ($P_2O_5$): calcium fluoride ($CaF_2$) was 44.7:44.7:34.0:16.2:0.5 on a weight basis, and subjected to a dry mixing process. The mixture was placed in a platinum crucible, and gradually heated to 1,500° C. After the mixture was maintained at this temperature for 2 hours, it was rapidly cooled to fabricate a second glass (CERA glass).

After the CBS glass and the CERA glass thus fabricated were pulverized into grains below 80 μm using a mortar and further pulverized in a planetary mill with zirconia balls for 5 hours to obtain glass powders having a particle diameter of 1~5 μm, respectively, the glass powders were mixed in alcohol for 12 hours in accordance with various mixing ratios (10~90% by weight) shown in Table 2 below.

After the glass powder mixture was completely dried, it was mixed with 1% PVA solution by weight to granulate the mixture. The granulated glass powder mixture was poured into a stainless steel mold and molded under an appropriate pressure to form a glass powder compacts. The glass powder compacts were sintered at 700~900° C. for 2 hours. The bulk density and the open porosity of the sintered specimens were measured at various temperatures, and the microstructures of the specimens were determined by electron microscopy.

FIG. 5 is a curve showing the shrinkage of some samples of Comparative Examples and Examples. As shown in FIG. 5, the specimen of Examples was completely densified at 750~830° C. The higher the content of CBS was, the lower the sintering temperature was. The bulk density and the open porosity of the specimens were measured. The results are shown in Table 2 below.

TABLE 2

Sintering temperature, maximum bulk density and crystallization temperature of each specimen

| | Mixing ratio | | Sintering | maximum | |
| | Cera glass (wt %) | CBS glass (wt %) | temperature (° C.) | bulk density (g/cm³) | crystallization temperature (° C.) |
|---|---|---|---|---|---|
| Comparative Example 1 (Cera glass) | 100 | 0 | 900 | 3.00 | 1000 |
| Example 4 | 95 | 5 | 900 | 2.98 | 950 |
| Example 5 | 90 | 10 | 850 | 2.96 | 900 |
| Example 6 | 75 | 25 | 800 | 2.93 | 750 |
| Example 7 | 50 | 50 | 800 | 2.84 | 800 |
| Example 8 | 25 | 75 | 800 | 2.79 | 750 |
| Example 9 | 10 | 90 | 800 | 2.75 | 750 |
| Example 10 | 5 | 95 | 750 | 2.72 | 750 |
| Comparative Example 2 (CSB) | 0 | 100 | 750 | 2.70 | 750 |

The maximum bulk density and the sintering temperature at which the maximum bulk density was obtained were proportional to the mixing ratio. In addition, the open porosity at the maximum bulk density was shown to be 0%. These results indicate that the densification was fully carried out.

Figure 6A:
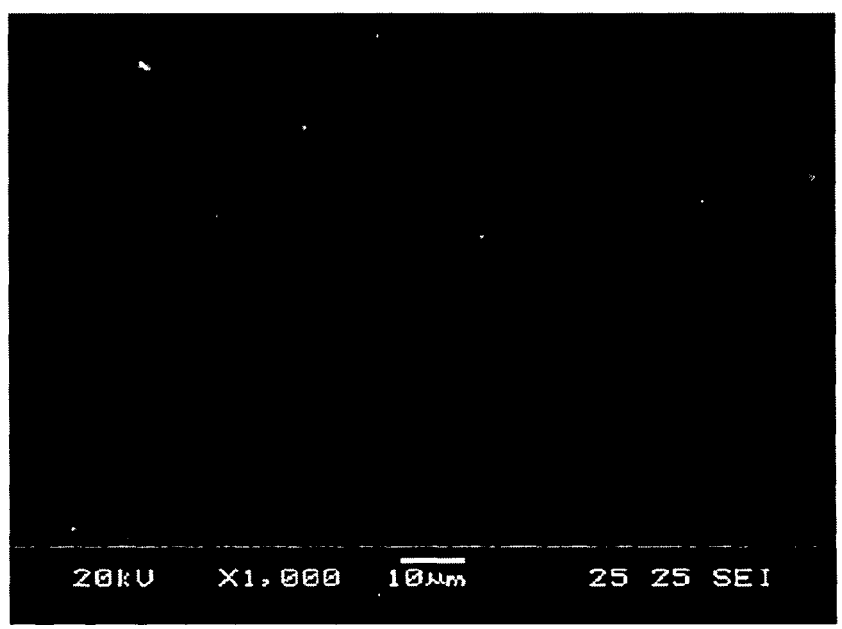
FIGS. 6a to 6e are electron microscope images showing the microstructures of specimens with the maximum bulk density, respectively.
Figure 6B:
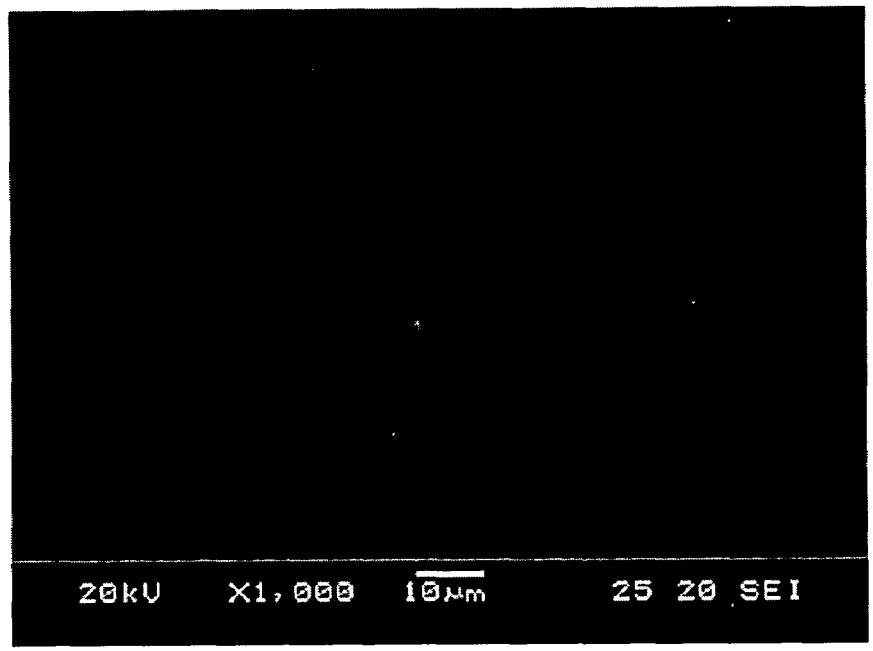
Figure 6C:
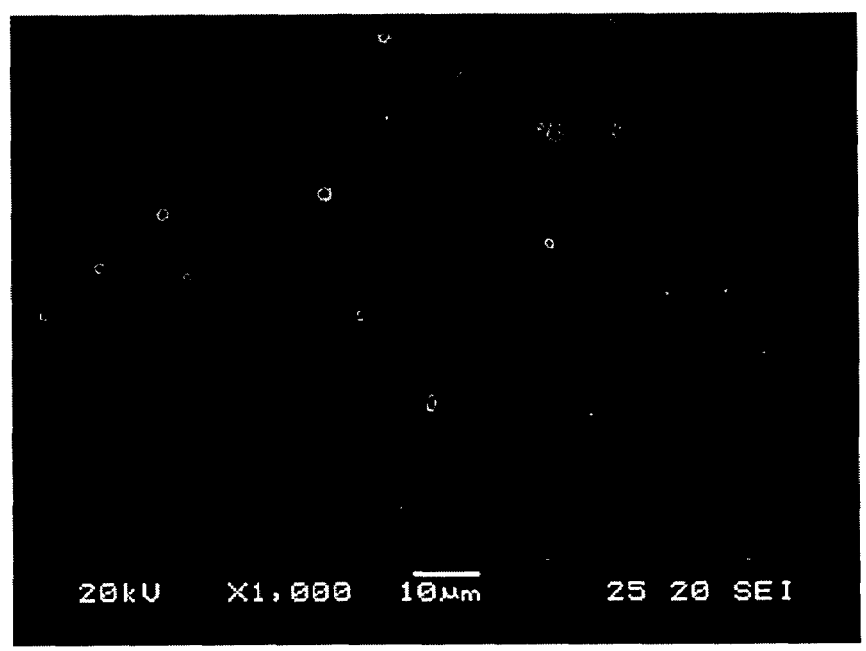
Figure 6D:
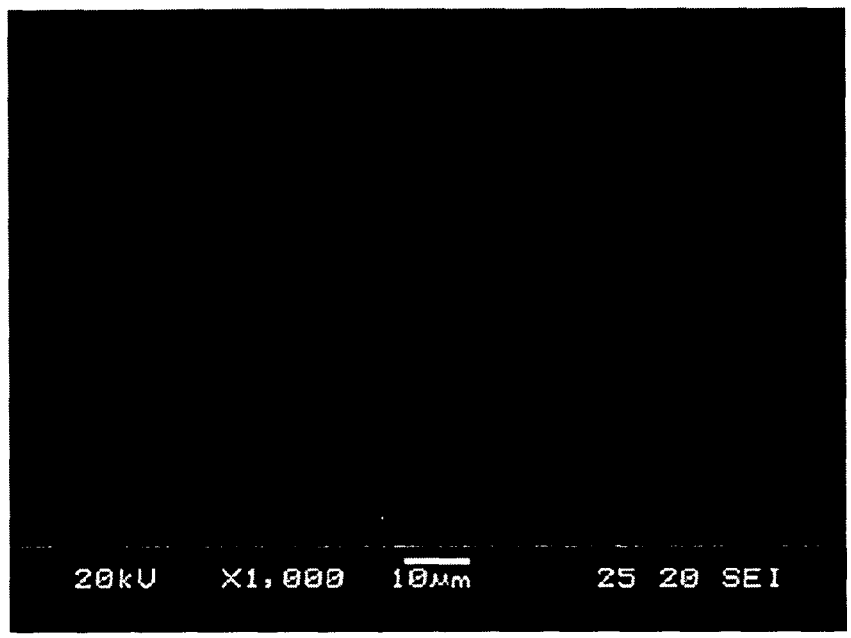

FIGS. 6a to 6e show electron microscope images of the sintered specimens of Comparative Examples and Examples, respectively. Specifically, the electron microscope images were obtained under the following conditions (Example No., mixing ratio of Cerabone-AW® to CBS, sintering temperature and sintering time):

FIG. 6a: Comparative Example 1, 100:0 (wt %), 900° C., 2 h;

FIG. 6b: Example 6, 75:25 (wt %), 800° C., 2 h;

FIG. 6c: Example 7, 50:50 (wt %), 800° C., 2 h;

FIG. 6d: Example 8, 25:75 (wt %), 800° C., 2 h; and

Figure 6E:
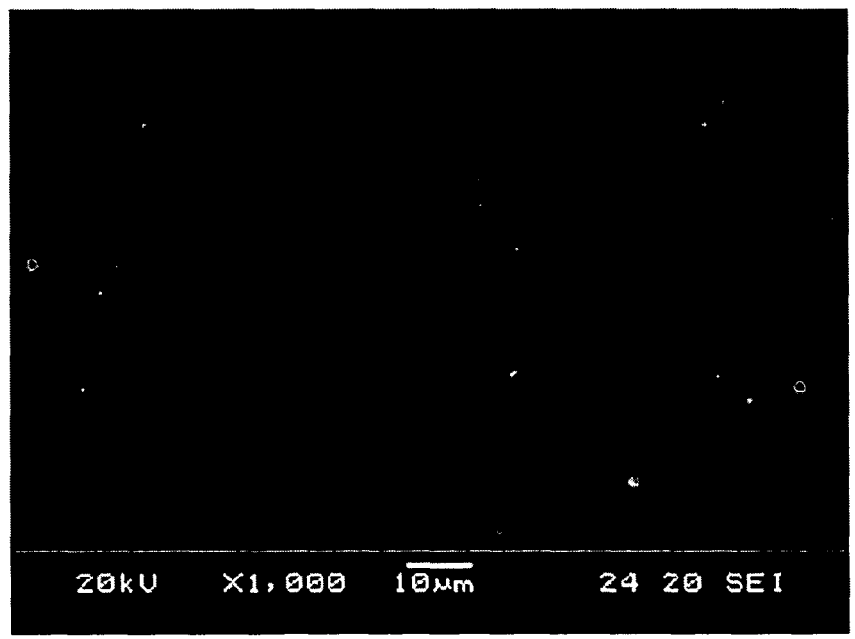

FIG. 6e: Comparative Example 2, 0:100 (wt %), 750° C., 2 h.

As can be seen from FIGS. 6a to 6e, few pores were observed in all specimens. It shows that all the specimens were fully densified. Although the change in crystallization temperature was not proportional to the mixing ratio, the complete crystallization temperature for Cerabone-AW® was as high as 1,000° C. but those for the mixtures of Cerabone-AW® and CBS glass were lower than 1,000° C.

Accordingly, the glass-ceramic having a composition identical to Cerabone-AW® must be sintered at a temperature as high as 1,050° C., but the glass-ceramics fabricated from the mixtures of Cerabone-AW® and CSB glass can be sintered at about 800° C., which is economically advantageous.

Figure 7A:
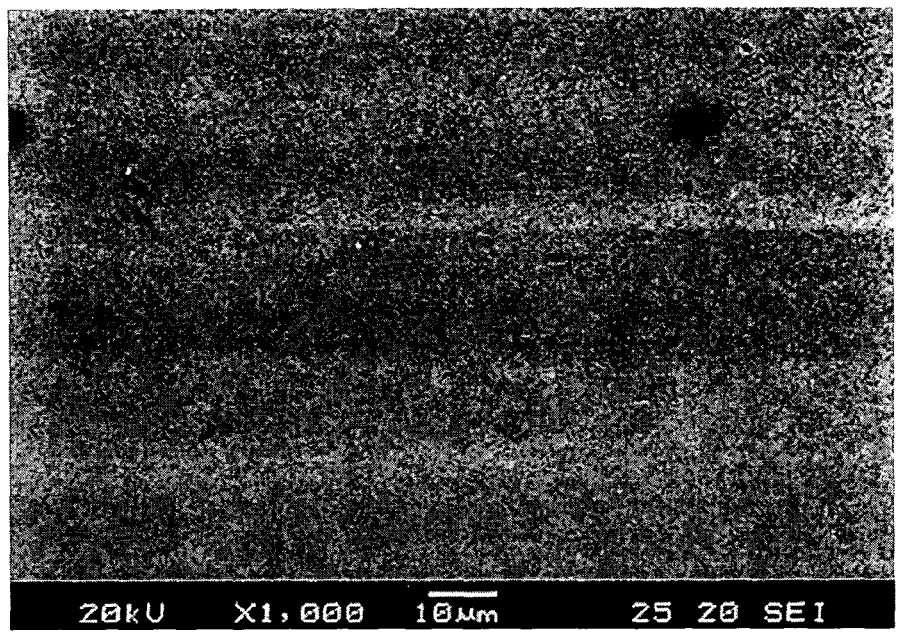
FIGS. 7a to 7f are electron microscope images showing the surfaces of specimens taken out 1 day after soaking polished specimens in simulated body fluid, respectively.
Figure 7B:
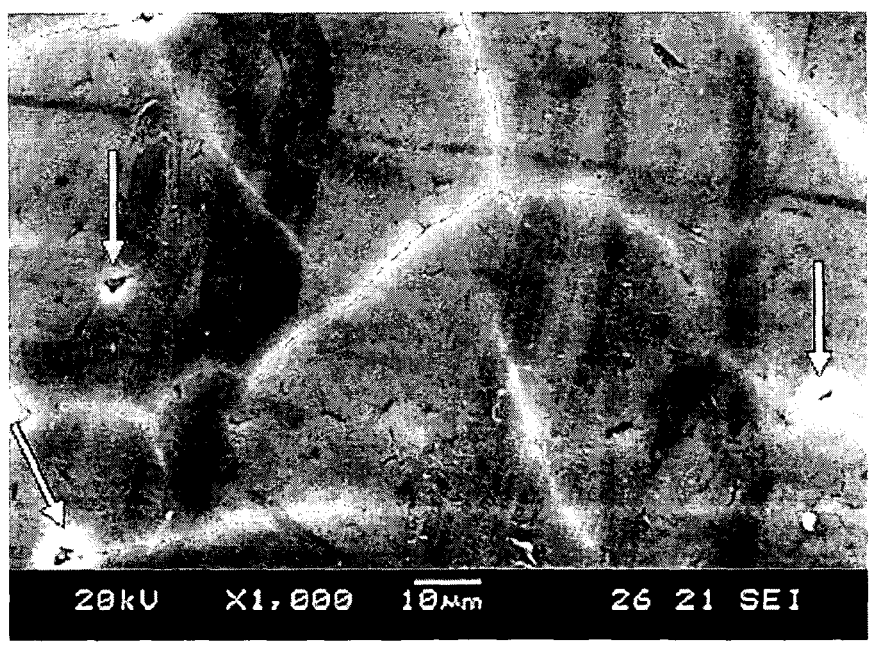
Figure 7C:
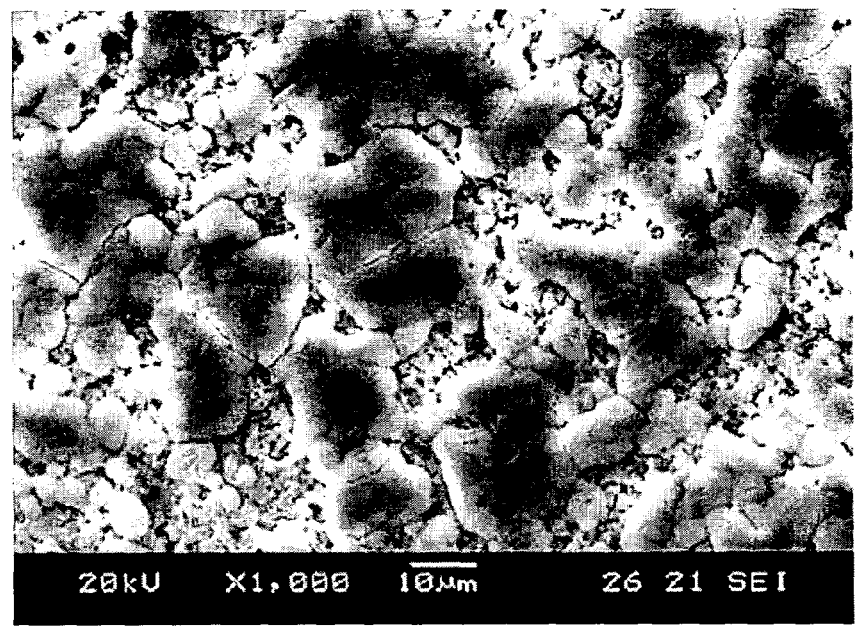
Figure 7D:
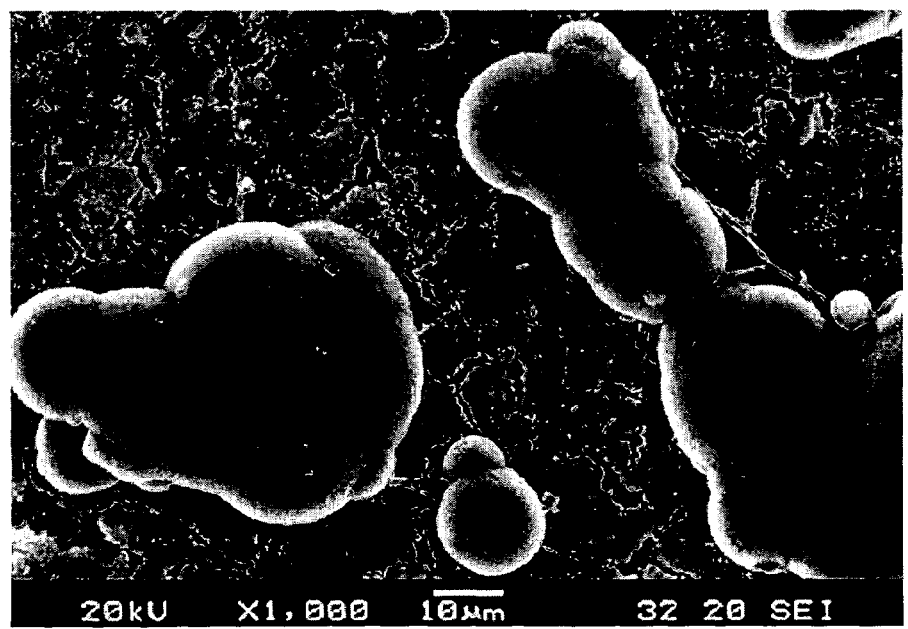
Figure 7E:
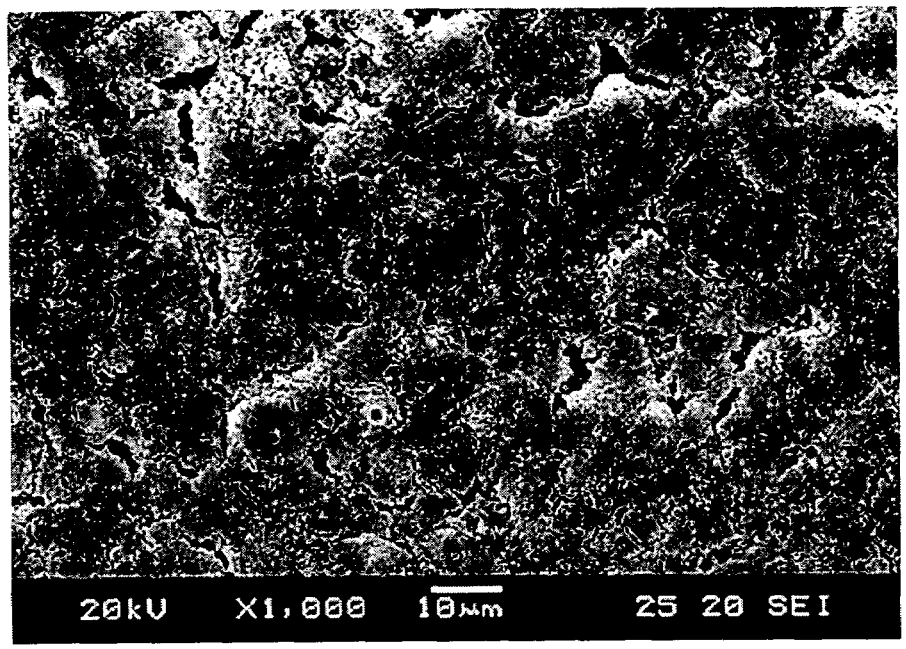
Figure 8:
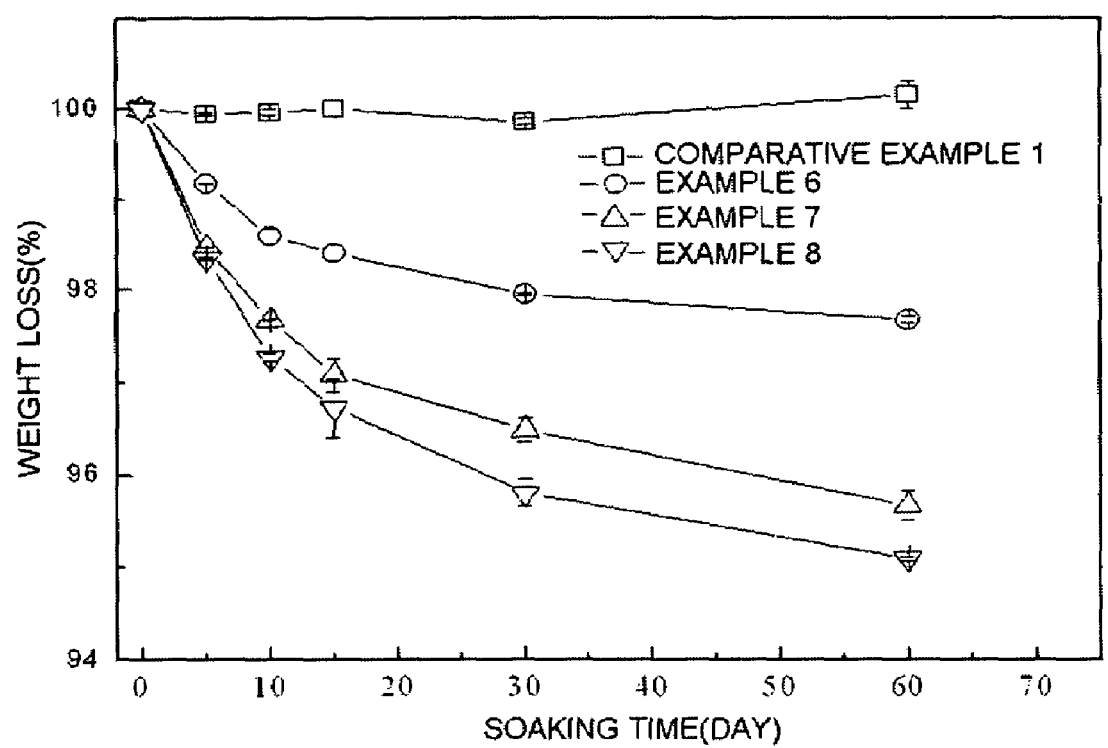
FIG. 8 is a graph showing the weight loss of specimens with increasing soaking time in simulated body fluid.

For bioactivity and biodegradation measurements, after some specimens were soaked in simulated body fluid, the surfaces of the specimens taken out of the simulated body fluid were observed by electron microscopy. The results were obtained under the following conditions (Example No., mixing ratio of Cerabone-AW® to CBS and soaking time):

FIG. 7a: Comparative Example 1, 100:0, 1 day;

FIG. 7b: Example 5, 90:10, 1 day;

FIG. 7c: Example 7, 50:50, 1 day;

FIG. 7d: Example 9, 10:90, 1 day;

FIG. 7e: Example 10, 5:95, 1 day; and

Figure 7F:
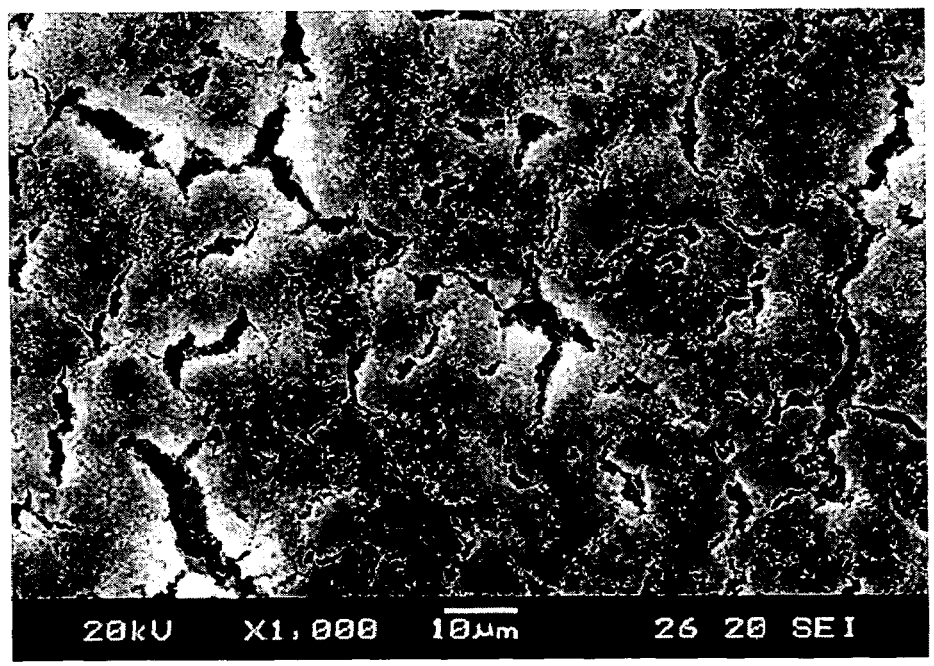

FIG. 7f: Comparative Example 2, 0:100, 1 day.

As shown in FIGS. 7a to 7f, as the content of CBS increased, the biodegraded zones increased in number. In addition, HCA layers indicating bioactivity were formed within 1 day after soaking in simulated body fluid, except for the specimens containing the CSB content of 90 wt % or higher. As shown in FIG. 8, as the content of CBS in the specimens increased, the weight of the specimens was greatly reduced due to the biodegradation.

The bioactivity evaluation on the specimens of Comparative Examples 1 and 2 and Examples was performed by soaking the specimens in 35 cc of simulated body fluid, and observing the surfaces of the specimens by electron microscopy.

As apparent from the above description, the present invention provides a composition and a method for solving disadvantages of poor biodegradation and high crystallization temperature and sintering temperature of conventional bioactive glass-ceramics. The composition and the method of the present invention can maintain constant bioactivity of glass-ceramics, and appropriately control the biodegradation rate of glass-ceramics.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A biodegradable and bioactive glass-ceramic fabricated from a composition consisting of: 41.40~45.75% by weight of calcium oxide (CaO), 35.0~47.62% by weight of silica ($SiO_2$), 0.50~14.58% by weight of boron oxide ($B_2O_3$), 0.46~4.14% by weight of magnesium oxide (MgO), 0.05~0.45% by weight of calcium fluoride ($CaF_2$) and 1.62~14.58% by weight of phosphorus pentoxide ($P_2O_5$).

* * * * *